United States Patent [19]

Kornblum et al.

[11] 4,012,498
[45] Mar. 15, 1977

[54] SUSTAINED RELEASE TABLET FORMULATIONS

[75] Inventors: Saul S. Kornblum, Springfield; Samuel B. Stoopak, West Caldwell, both of N.J.

[73] Assignee: Sandoz, Inc., E. Hanover, N.J.

[22] Filed: Feb. 19, 1976

[21] Appl. No.: 655,838

Related U.S. Application Data

[63] Continuation-in-part of Ser. No. 455,185, March 27, 1974, abandoned.

[52] U.S. Cl. .................................. 424/22; 424/19; 424/20
[51] Int. Cl.[2] ...................... A61K 9/22; A61K 9/26
[58] Field of Search ............................... 424/19–22

[56] References Cited

UNITED STATES PATENTS

| | | | |
|---|---|---|---|
| 2,953,497 | 9/1960 | Press | 424/19 |
| 3,044,938 | 7/1962 | Halley | 424/19 |
| 3,079,303 | 2/1963 | Raff et al. | 424/33 |
| 3,146,168 | 8/1964 | Battista | 424/361 |

*Primary Examiner*—Shep K. Rose
*Attorney, Agent, or Firm*—Gerald D. Sharkin; Robert S. Honor; Walter F. Jewell

[57] ABSTRACT

This invention provides controlled, e.g., sustained release of drugs from medicament formulations containing a plurality of medicaments, wherein a desirable release pattern is maintained for both low concentration and high concentration drugs of the formulation.

12 Claims, No Drawings

SUSTAINED RELEASE TABLET FORMULATIONS

This application is a continuation-in-part of application, Ser. No. 455,185, filed Mar. 27, 1974, now abandoned.

This invention relates to controlled release medicament formulations. More particularly, it relates to the controlled release of low concentration and high concentration drugs from medicament formulations.

Most prior art sustained release matrices rely upon dissolution of the soluble portions (lactose, succrose, etc.) of a tablet to form channels within the matrix, so that body fluids (e.g., gastrointestinal fluids) can migrate in and out of the matrix. Thus the drug dissolves in the body fluids diffusing into the tablet which then diffuses from the tablet into the gastrointestinal tract for subsequent drug absorbtion.

In those prior art controlled release formulations which contain a plurality of drugs wherein one of the drugs has a lower concentration than the other drugs, it is difficult to maintain a desirable release pattern for the low-concentration drug, especially if it has relatively good solubility in gastric fluid.

The prior art formulations in using only vinylacetatevinyl alcohol copolymer (processed) as a retardant have proven to be unacceptable in retarding the low concentration drugs of the formulations.

It is, therefore, an object of this invention to provide controlled release of low concentration drugs from medicament formulations containing a plurality of medicaments wherein the release rates for individual drugs are controllable, regardless of their concentration or solubility in the formulation.

This and other objects of this invention will become apparent from the following detailed description and examples.

This invention provides controlled release medicament formulations containing a plurality of drugs wherein one or more drugs having the lowest concentration of the drugs of the formulation is separately incorporated in a controlled release matrix.

The low concentration drug-controlled release matrix of this invention is one that is affected by changes in pH, e.g., drug release is effected in a basic medium. Among the materials which may be used as a controlled release matrix are cellulose acetate phthalate (CAP), polyvinyl acetate phthalate, hydroxypropylmethyl cellulose phthalate, and the like. It is a preferred embodiment of this invention to include in the controlled release matrix insoluble salts of calcium or barium, such as calcium sulfate-dihydrate (terra alba), barium sulfate, and the like. It is also preferred to include in the controlled release matrix cellulose materials, such as microcrystalline cellulose, and the like.

The concentration of the drug or drugs incorporated in the controlled release matrix may each be from about 1/10 to 1/1000, preferably 1/100 to 1/300 of that of the total concentration of the other drugs in the other controlled release portion formulation.

This invention will be described by way of examples with regard to a two-drug component, e.g., phenobarbital and Bellafoline, three-portion controlled release medicament, and a three-drug component, e.g., ergotamine phenobarbital and Bellafoline, three-portion controlled release medicament. The Bellafoline and ergotamine are in a lower concentration than the phenobarbital. However, it will be understood by those skilled in the art that the invention is also applicable to controlled release systems which contain four or more drug components.

EXAMPLE 1

Controlled release tablet formulations of the present invention and the prior art were prepared containing the following ingredients:

| INGREDIENTS | PRESENT INVENTION (PARTS) | PRIOR ART (PARTS) |
|---|---|---|
| Bellafoline[1] | 0.250 | 0.250 |
| Phenobarbital, U.S.P. | 50.000 | 50.000 |
| Vinyl Acetate-Vinyl Alcohol[2] copolymer (Processed) Resin | 36.667 | 30.000 |
| Stearic Acid, U.S.P. | 18.667 | 3.333 |
| Lactose, U.S.P. | 88.242 | 124.618 |
| Succrose, U.S.P. | 31.667 | 50.083 |
| Gelatin, U.S.P. | 1.333 | 1.333 |
| Calcium Sulfate-Dihydrate (Terra Alba) | 18.333 | — |
| Cellulose Acetate Phthalate | 2.500 | — |
| Microcrystalline Cellulose | 11.958 | — |
| F.D. & C. Yellow No. 6, Cert. | 0.133 | 0.133 |
| F.D. & C. Green Blend 201 Cert. | 0.250 | 0.250 |
| TOTAL | 260.000 | 260.000 |

[1]Levoratory alkaloids of belladonna
[2]Bakelite vinyl Resin AYAC, Union Carbide The tablets were prepared by separately preparing a green, orange, and white granulation, blending equal portions of each granulation and then compressing the blended granulations into tablets. The formulation and procedure for preparing each of the green, orange, and white granulations is as follows:

| GREEN GRANULATION INGREDIENTS | PRESENT INVENTION PER 260 PARTS | PRIOR ART PER 260 PARTS |
|---|---|---|
| Bellafoline Substance 60%[3] | 0.954 | 20.00[4] |
| Phenobarbital U.S.P. Powder | 50.000 | 60.00 |
| Vinyl Acetate-Vinyl Alcohol Copolymer (Processed) Resin | 60.000 | 50.00 |
| Stearic Acid, U.S.P. Powder | 50.000 | 4.00 |
| Calcium Sulfate, Dihydrate | 55.000 | — |
| Microcrystalline Cellulose | 35.796 | — |
| F.D. & C. Green Blend 201 Cert. | 0.750 | 0.750 |
| Cellulose Acetate Phthalate | 7.500 | — |
| Lactose U.S.P. | — | 70.00 |
| Succrose Powdered U.S.P. | — | 55.25 |
| GRANULATING LIQUIDS | | |
| Acetone | q.s. | — |
| Alcohol, S.D. No. 30 | q.s. | q.s. |
| Purified Water | q.s. | q.s. |

[3]Bellafoline 60%, Lactose 40%
[4]Bellafoline Trituration 1½% as the malate

Procedure for Preparing the Green Granulation of the Present Invention

Weigh and dissolve the Cellulose Acetate Phthalate (CAP) in a mixture of 1.2 liters (L.) of Acetone and 1.2 L. of S.D. No. 30 Alcohol; Weigh and disperse the Bellafoline Substance 60% in 0.2 L. of S.D. No. 30 Alcohol; add the Bellafoline Substance 60% - S.D.A No. 30 mixture to the Cellulose Acetate Phthalate Solution and mix well until a uniform mixture is obtained.

Weigh the Phenobarbital, Processed AYAC [1/2% Colloidal Silicon Dioxide (Cab-o-sil)], Microcrystalline Cellulose, and Calcium Sulfate Dihydrate; Screen through a No. 20 Mesh Stainless Steel Screen, and place in the Lodige Mixer, Weigh the Stearic Acid and Green Blend 201 and bolt through a No. 60 mesh cloth; then add to the Lodige Mixer. Mix for two minutes at 160 RPM with plows and chopper.

Add 1.8 L. of Purified Water to the well-mixed powders and mix for two minutes at 160 RPM with plows and chopper.

Add about half the Bellafoline - CAP mixture and mix for 30 seconds at 160 RPM with plows and chopper.

Add the remainder of the Bellafoline - CAP mixture and mix until the desired granulation is obtained (open mixer at 30 second intervals to observe granulation - Total time: 90 seconds).

Spread the wet granulation on paper-lined trays and dry in a vacuum oven at 35° – 40° C. for 2 hours to overnight depending upon wetness of mass.

Pass the dry granulation through a No. 14 Mesh Stainless Steel Screen employing a Frewitt Oscillating granulator, and then pass over a No. 35 Mesh Stainless Steel employing the Sweco Vibrator to remove "fines".

Procedure for Preparing the Green Granulation of the Prior Art

Weigh and screen the ingredients through a 14 × 14 mesh screen and transfer into a Glen Mixer for 20 to 30 minutes at 40 RPM. To the first 130 parts of the mixture gradually add 3.0 parts of purified water and mix for 10 to 15 minutes at 40 – 80 RPM until the color appears. At this point, reduce the speed to 40 RPM and add 3.0 parts of S.D. No. 30 alcohol and gradually increase the speed to 100 RPM. Mix until a proper consistency is obtained. The mixture is then granulated in a Tornado Mill using a one-half inch screen at low speed with the knives forward. The granulation is dried in a vacuum dryer for 10 hours at 45° to 50° C. the above is then repeated for the second 130 parts and the entire dried granulation is screened to the desired mesh (14 – 35 mesh) size using a Oscillator, Tornado Mill, and Cirlyptic Sifter.

| INGREDIENTS | ORANGE GRANULATION PRESENT INVENTION PER 260 PARTS | PRIOR ART PER 260 PARTS |
|---|---|---|
| Bellafoline Substnce 60% | 0.25 | 15.00[4] |
| Phenobarbital, U.S.P. Powder | 55.00 | 45.00 |
| Vinyl Acetate-Vinyl Alcohol Copolymer (Processed) Resin | 50.00 | 24.00 |
| Stearic Acid, U.S.P., Powder | 3.00 | 1.80 |
| Lactose, U.S.P., Powder | 76.35 | 81.60 |
| Succrose, U.S.P., Powder | 75.00 | 75.00 |
| F.D. & C. Yellow No. 6, Cert. | 0.40 | 0.40 |
| GRANULATING LIQUIDS | | |
| Alcohol, Specially Denatured No. 30 | q.s. | q.s. |
| Acetone | q.s. | — |
| Purified Water, U.S.P. | q.s. | q.s. |

[4]Bellafoline Trituration I 1.2% as the malate

Procedure for Preparing the Orange Granulation of the Present Invention

Weigh 10% of Processed AYAC [1/2% Colloidal Silicon Dioxide (Cab-o-sil)] and dissolve in 0.75 L. of Acetone; weigh the Bellafoline substance 60% and dissolve in 500 ml. of S.D. No. 30 Alcohol; then add the Bellafoline-S.D. No. 30 Alcohol mixture to the AYAC - Acetone solution and mix well until a uniform mixture is obtained.

Weigh the Phenobarbital, Lactose, Succrose, add the remaining 90% of Processes AYAC, and pass through a No. 20 Mesh Stainless Steel Screen; then transfer to an AMF Planetary Mixer; weigh the Stearic Acid and F.D. & C. Yellow No. 6 and bolt through a No. 60 mesh cloth; then add to the AMF Mixer and mix well for 20 minutes.

Add 2.0 L. of Purified Water to the well-mixed powders and continue mixing until the orange color appears.

Granulate by slowly adding the Bellafoline - AYAC mixture from Step No. 1. (Additional S.D. No. 30 Alcohol may be used if necessary to obtain a granulation).

Spread the wet granulation on paper-lined trays and dry in a vacuum oven at 35° – 40° C. for 2 hours to overnight depending upon wetness of the mass.

Pass the dry granulation through a No. 14 Mesh Stainless Steel Screen employing the Frewitt Oscillating Granulator; then pass over a No. 35 Mesh Stainless Steel Screen employing the Sweco Vibrator to remove "fines".

Procedure for Preparing the Orange Granulation of the Prior Art is the same as that described for the prior art green granulation.

| INGREDIENTS | WHITE GRANULATION PRESENT INVENTION PER 260 PARTS | PRIOR ART PER 260 PARTS |
|---|---|---|
| Bellafoline Trituration[4] 1½% | 5.0 | 15.0 |
| Phenobarbital, U.S.P., Powder | 45.0 | 45.0 |
| Stearic Acid, U.S.P., Powder | 3.0 | 3.0 |

[4]As the malate

Procedure for Preparing the White Granulation of the Present Invention

Weigh the Bellafoline Trituration, Phenobarbital, Stearic Acid, Lactose, and Succrose, pass through a No. 18 Mesh Stainless Steel Screen; then place in a Hobart Planetary Mixer and mix for 20 minutes.

Weigh and Dissolve the gelatin in 300 ml. of warm Purified Water.

Granulate, using the above gelatin solution and 275 ml. of S.D. No. 30 Alcohol.

Spread the wet granulation on paper-lined trays and dry overnight in a regular drying oven at 40° – 45° C.

Pass the dry granulation through a No. 14 Mesh Stainless Steel Screen employing the Frewitt Oscillating Granulator; then pass over a No. 35 Mesh Stainless Steel Screen employing the Sweco Vibrator to remove "fines".

Procedure for Preparing the White Granulation of the Prior Art

The ingredients are weighed and screened through a 14 × 14 mesh screen. The Gelatin is dissolved in the purified water with heat until clear and then warm S.D.

No. 30 alcohol is added with constant stirring. The gelatin-water-alcohol solution is added to the other ingredients and mixed for 15 minutes. The mixture is then granulated through an 18 × 18 mesh screen on an oscillator and dried for 10 hours at 45° C. The dried granulation is then pressed through an oscillator equipped with a 14 × 14 mesh screen and then sifted to obtain 14 – 35 mesh size granules.

Tablets were prepared by weighing equal quantities of the Green, Orange, and White Granulations, tumbling them in a Patterson Kelley Twin Sheel Blender for 15 minutes (no Intensifier) and then compressing the resulting granulation into tablets using a suitable rotary tablet press. The final tablets contained the following portions of each granulation:

| COMPOSITION | PRESENT INVENTION PER 260 PART TABLET | PRIOR ART PER 260 PART TABLET |
| --- | --- | --- |
| Green Granulation | 86.66 parts | 86.66 parts |
| Orange Granulation | 86.66 parts | 86.66 parts |
| White Granulation | 86.66 parts | 86.66 parts |

| Physical Parameters of Prepared Tablets | | |
| --- | --- | --- |
| | PRESENT INVENTION | PRIOR ART |
| Tablet Color: | White, Orange, and Green | White, Orange, and Green |
| Tablet Weight: | 260 mg. | 260 mg. |
| Tablet Thickness: | 2.6 mm. | 2.6 mm. |
| Tablet Hardness: (Strong Cobb Apparatus) | 10 – 14 kg. | 10 – 14 kg. |
| Tablet Diameter: | 10 mm. | 10 mm. |

EXAMPLE 2

Controlled release tablet formulations of the present invention and the prior art were prepared containing the following ingredients:

| INGREDIENTS | PRESENT INVENTION MG. PER TABLET | PRIOR ART MG. PER TABLET |
| --- | --- | --- |
| Bellafoline[1] | 0.200 | 0.200 |
| Ergotamine Tartrate, U.S.P. | 0.600 | 0.600 |
| Phenobarbital, U.S.P. | 40.000 | 40.000 |
| Vinyl Acetate-Vinyl Alcohol[2] Copolymer (Processed) Resin | 36.667 | 30.000 |
| Stearic Acid, U.S.P. | 18.667 | 3.000 |
| Lactose, U.S.P. | 95.592 | 175.98 |
| Succrose, U.S.P. | 31.667 | 6.666 |
| Gelatin, U.S.P. | 1.333 | 1.066 |
| Tartaric Acid, N.F. | 2.000 | 2.000 |
| Calcium Sulfate-Dihydrate (Terra Alba) | 18.333 | — |
| Cellulose Acetate Phthalate | 2.500 | — |
| Microcrystalline Cellulose | 11.958 | — |
| F.D. & C. Yellow No. 5, Cert. | 0.100 | 0.100 |
| F.D. & C. Yellow No. 6, Cert. | 0.133 | 0.133 |
| F.D. & C. Green Blend 201 Cert. | 0.250 | 0.250 |
| TOTAL | 260.000 | 260.000 |

[1] Levoratory alkaloids of belladonna
[2] Bakelite Vinyl Resin AYAC, Union Carbide The tablets were prepared by separately preparing a green, orange, and yellow granulation, blending equal portions of each granulation and then compressing the blended granulations into tablets. The formulation and procedure for preparing each of the green, orange, and yellow granulations is as follows:

| GREEN GRANULATION INGREDIENTS | PRESENT INVENTION PER 260 PARTS | PRIOR ART PER 260 PARTS |
| --- | --- | --- |
| Bellafoline Substance 60%[3] | 0.717 | 16.00[4] |
| Ergotamine Tartrate[5] Trituration | 12.900 | 7.20 |
| Phenobarbital, U.S.P. Powder | 36.000 | 48.00 |
| Tartaric Acid, N.F. | 2.000 | 2.00 |
| Vinyl Acetate-Vinyl Alcohol Copolymer (Processed) Resin | 60.000 | 50.00 |
| Stearic Acid, U.S.P. Powder | 50.000 | 3.00 |
| Calcium Sulfate, Dihydrate | 54.100 | — |
| Microcrystalline Cellulose | 35.796 | — |
| F.D. & C. Green Blend 201 Cert. | 0.750 | 0.750 |
| Cellulose Acetate Phthalate | 7.500 | — |
| Lactose, U.S.P. | — | 133.05 |
| GRANULATION LIQUIDS | | |
| Acetone | q.s. | — |
| Alcohol, S.D. No. 30 | q.s. | q.s. |
| Purified Water | q.s. | q.s. |

[3] Bellafoline 60%, Lactose 40%
[4] Bellafoline Trituration 1½% as the malate
[5] Ergotamine Trituration 10% as the tartrate

Procedure for Preparing the Green Granulation of the Present Invention

Weigh and dissolve the Cellulose acetate phthalate (CAP) in a mixture of 1.2 L. of acetone and 1.2 L. of S.D. No. 30 alcohol; weigh and disperse and the Bellafoline substance 60% and ergotamine trituration 10% in 0.2 L. of S.D. No. 30 alcohol; add the bellafoline substance 60% ergotamine trituration 10% – S.D. No. 30 mixture to the cellulose acetate phthalate solution and mix well until a uniform mixture is obtained.

Weigh the phenobarbital, processed AYAC [1/2% Colloidal Silicon Dioxide (Cab-o-sil)], microcrystalline cellulose, and calcium sulfate dihydrate; screen thorugh a No. 20 mesh stainless steel screen, and place in the Lodige Mixer. Weigh the Stearic acid and Green Blend 201 and bolt through a No. 60 mesh cloth; then add to the Lodige Mixer. Mix for two minutes at 160 RPM with plows and chopper.

Add 1.8 L. of purified water to the well-mixed powders and mix for two minutes at 160 RPM with plows and chopper.

Add about half the Bellafoline ergotamine-CAP mixture and mix for 30 seconds at 160 RPM with plows and chopper.

Add the remainder of the Bellafoline-ergotamine-CAP mixture and mix until the desired granulation is obtained (open mixer at 30-second intervals to observe granulation - total time: 90 seconds).

Spread the wet granulation on paper-lined trays and dry in a vacuum oven at 35° – 40° C. for 2 hours to overnight depending upon wetness of the mass.

Pass the dry granulation through a No. 14 mesh stainless steel screen employing a Frewitt Oscillating granulator, and then pass over a No. 35 mesh stainless steel screen employing the Sweco Vibrator to remove "fines."

Procedure for Preparing the Green Granulation of the Prior Art

Weigh and screen the ingredients through a 14 × 14 mesh screen and transfer into a Glen Mixer for 20 to 30 minutes at 40 RPM. To the first 130 parts of the mixture gradually add 3.0 parts of purified water and mix for 10 to 15 minutes at 40 – 80 RPM until the color appears. At this point, reduce the speed to 40 RPM and add 3.0 parts of S.D. No. 30 alcohol and gradually increase the speed to 100 RPM. Mix until a proper consistency is obtained. The mixture is then granulated in a Tornado Mill using a one-half inch screen at low speed with the knives forward. The granulation is dried in a vacuum dryer for 10 hours at 45° to 50° C. The above is then repeated for the second 130 parts and the entire dried granulation is screened to the desired mesh (14 – 35 mesh) size using an Oscillator, Tornado Mill, and Cirlyptic Sifter.

| ORANGE GRANULATION | | |
| --- | --- | --- |
| INGREDIENTS | PRESENT INVENTION PER 260 PARTS | PRIOR ART PER 260 PARTS |
| Bellafoline substance 60% | 0.188 | 14.00[4] |
| Ergotamine trituration | 3.387 | 6.30 |
| Phenobarbital, U.S.P., Powder | 44.1 | 42.00 |
| Tartaric Acid, N.F. | — | 2.00 |
| Vinyl Acetate-Vinyl Alcohol Copolymer (Processed) Resin | 50.00 | 40.00 |
| Stearic Acid, U.S.P., Powder | 3.00 | 3.00 |
| Lactose, U.S.P., Powder | 83.93 | 152.30 |
| Succrose, U.S.P. Powder | 75.00 | — |
| F.D. & C. Yellow No. 6, Cert. | 0.40 | 0.40 |
| GRANULATING LIQUIDS | | |
| Alcohol, Specially Denatured NO. 30 | q.s. | q.s. |
| Acetone | q.s. | — |
| Purified Water, U.S.P. | q.s. | q.s. |

[4]Bellafoline Trituration 1 1.2% as the malate

Procedure for Preparing the Orange Granulation of the Present Invention

Weigh 10% of processed AYAC [1/2% Coolidal Silicon Dioxide (Cab-o-sil)] and dissolve in 0.75 L. of acetone; weigh the Bellafoline substance 60% and Ergotamine Trituration 10% and dissolve in 500 ml. of S.D. No. 30 alcohol; then add the Bellafoline-Ergotamine-S.D. No. 30 alcohol mixture to the AYAC-acetone solution and mix well until a uniform mixture is obtained.

Weigh the phenobarbital, lactose, succrose, and the remaining 90% of processed AYAC, and pass through a No. 20 mesh stainless steel screen; then transfer to an AMF Planetary Mixer; weigh the Stearic Acid and F.D. & C. Yellow No. 6 and bolt through a No. 60 mesh cloth; then add to the AMF Mixer and mix well for 20 minutes.

Add 2.0 L. of purified water to the well-mixed powders and continue mixing until the orange color appears.

Granulate by slowly adding the Bellafoline-ergotamine-AYAC mixture from Step No. 1. (Additional S.D. No. 30 alcohol may be used if necessary to obtain a granulation).

Spread the wet granulation on paper-lined trays and dry in a vacuum oven at 35° – 40° C. for 2 hours to overnight depending upon wetness of the mass.

Pass the dry granulation through a No. 14 mesh stainless steel screen employing the Frewitt Oscillating Granulator; then pass over a No. 35 mesh stainless steel screen employing the Sweco Vibrator to remove "fines".

Procedure for Preparing the Orange Granulation of the Prior Art is the same as that described for the prior art green granulation.

| YELLOW GRANULATION | | |
| --- | --- | --- |
| INGREDIENTS | PRESENT INVENTION PER 260 PARTS | PRIOR ART PER 260 PARTS |
| Bellafoline Trituration[4] 1½percent | 3.760 | 10.0 |
| Ergotamine Trituration | 1.692 | 4.5 |
| Phenobarbital, U.S.P. Powder | 39.900 | 30.0 |
| Tartaric Acid, N.F. | — | 2.0 |
| Stearic Acid, U.S.P., Powder | 3.000 | 3.0 |
| Gelatin, U.S.P. | 4.000 | 3.2 |
| Lactose, U.S.P., Powder | 187.400 | 187.0 |
| Succrose, U.S.P., Powder | 20.000 | 20.0 |
| F.D. & C. Yellow No. 5, Cert. | 0.300 | 0.3 |
| GRANULATING LIQUIDS | | |
| Alcohol, Specially Denatured | q.s. | q.s. |
| Purified Water, U.S.P. | q.s. | q.s. |

[4]As the malate

Procedure for Preparing the Yellow Granulation of the Present Invention

Weigh the Bellafoline Trituration, ergotamine Trituration, phenobarbital, stearic acid, lactose, and sucrose, pass through an No. 18 mesh stainless steel screen; then place in a Hobart Planetary Mixer and mix for 20 minutes.

Weigh and dissolve the gelatin in 300 ml. of warm purified water.

Granulate, using the above gelatin solution and 275 ml. of S.D. No. 30 alcohol.

Spread the wet granulation on paper-lined trays and dry overnight in a regular drying oven at 40° – 45° C.

Pass the dry granulation through a No. 14 mesh stainless steel screen employing the Frewitt Oscillating Granulator; then pass over a No. 35 mesh stainless steel screen employing the Sweco Vibrator to remove "fines".

Procedure for Preparing the Yellow Granulation of the Prior Art

The ingredients are weighed and screened through a 14 × 14 mesh screen. The gelatin is dissolved in the purified water with heat until clear and then warm S.D. No. 30 alcohol is added with constant stirring. The gelatin-water-alcohol solution is added to the other ingredients and mixed for 15 minutes. The mixture is then granulated through an 18 × 18 mesh screen on an oscillator and dried for 10 hours at 45° C. The dried granulation is then pressed thorugh an oscillator equipped with a 14 × 14 mesh screen and then sifted to obtain 14– 35 mesh size granules.

Tablets were prepared by weighing equal quantities of the green, orange, and white granulations, tumbling them in a Patterson Kelley Twin Shell Blender for 15 minutes (no Intensifier) and then compressing the resulting granulation into tablets using a suitable rotary tablet press. The final tablets contained the following portions of each granulation:

| COMPOSITION | PRESENT INVENTION PER 260 PART TABLET | PRIOR ART PER 260 PART TABLET |
|---|---|---|
| Green granulation | 86.66 parts | 86.66 parts |
| Orange granultion | 86.66 parts | 86.66 parts |
| Yellow granulation | 86.66 parts | 86.66 parts |

Physical Parameters of Prepared Tablets

|  | PRESENT INVENTION | PRIOR ART |
|---|---|---|
| Tablet Color: | Yellow, Orange, and Green | Yellow, Orange, and Green |
| Tablet Weight: | 260 mg. | 260 mg. |
| Tablet Thickness: | 2.6 mm. | 2.6 mm. |
| Tablet Hardness: (Strong Cobb Apparatus) | 10 – 14 kg. | 10 – 14 kg. |
| Tablet Diameter: | 10 mm. | 10 mm. |

EXAMPLE 3

Tablets prepared as described in Example 1 were tested for the dissolution rate of phenobarbital and Bellafoline.

1. Release of Bellafoline

Place the tablets in a disintegration basket separating the tablets in each tubes with wire mesh partitions.

Place 800 ml. of simulated gastric fluid T.S. without pepsin (SGF) (USP XVIII)[1] in a 100 ml. beaker, and allow the solution to reach the temperature of 37° ± 2° C.

[1] U.S. Pharmacopeia

Attach the basket to the disintegration apparatus and operate it for 2 hours in the SGF.

At the end of 2 hours, stop the apparatus, withdraw 50.0 ml. and adjust the volume to 800 ml. with SGF. Withdraw 2 × 200.0 ml., and replace the volume with simulated intestinal fluid T.S. without enzyme (SIF) and (USP XVIII) previously warmed up to 37° C., 200.0 ml. of the withdrawn solution is kept for the assay. Start the apparatus again and operate it for another 2 hours.

At the end of the third hour, adjust the volume to 800 ml. with 20.0 ml. of SIF and withdraw 200.0 ml. for the assay, adjust the volume to 800 ml. with SIF at the end of the fourth hour, adjust the volume to 800 ml. with 20.0 ml. SIF and withdraw 200.0 for assay.

Each sample withdrawn is transferred to an appropriate separatory funnel and made alkaline with 3 ml. of concentrated ammonium hydroxide. Extract gently with three 20 ml. portions of chloroform, combine the extracts in a 125 ml. separatory funnel. Add 10 ml. of distilled water and shake for about 1 minute. Allow the layers to separate well and transfer the chloroform layer into a third separatory funnel. Extract the water layer with 5 ml. of chloroform and add this chloroform to the combined chloroform extracts.

To the chloroform solution, add 20.0 ml. of alcoholic acetic solution and duplicate 5.0 aliquots of the standard solution into separate small evaporating dishes. Carefully evaporate the solutions to dryness on a steam bath, avoiding any excess heat.

Add 0.8 ml. of fuming nitric acid and evaporate to dryness again. Remove the dishes from the heat immediately after the evaporation is completed, and cool them to room temperature in a desiccator.

Pipet 15.0 ml. of dimethylformamide (Spectrophotmetric grade Baker No. 9222) into each dish and dissolve the residue completely.

Pipet 10.0 ml. of each solution in a test tube and add to each tube 1.0 ml. of 10% tetraethylammonium hydroxide in distilled water.

Determine the absorbances of the resulting solutions in a suitable spectrophotmeter at 550 m$\mu$ after exactly 5 minutes, against a bland (10 ml. of dimethylformamide plus 1.0 ml. of 10% tetraethylammonium hydroxide in water).

Average the sample readings and the standard readings.

2. Assay of the Bellafoline in the Residue

After the 4-hour sample was withdrawn, filter the entire solution through a Buchner funnel. Wash the disintegration apparatus with distilled water in order to get all the leftover particles from the tablet onto the funnel. Dry the residue overnight (protected from light), and grind it to a fine powder.

Quantitatively transfer the powder into a 250 ml. separatory funnel with the aid of two 25.0 ml. portions of 0.1 N NH$_4$OH. Add 150.0 ml. of 0.1 N NH$_4$OH to the separatory funnel. Shake for 15 minutes and proceed in a similar manner as described in 1), extracting the alkaline layer with 3 × 20 ml. of chloroform but using 25.0 ml. of alcoholic acetic acid solution for the last extraction, and taking 2.0 ml. aliquots of the sample alcoholic acetic acid solution, and 5.0 ml. aliquots of the standard alcoholic acetic acid solution for evaporation.

3. Release of Phenobarbital

Place the tablets in a disintegration basket. Immerse it into a beaker containing 800 ml. of SGF and proceed with the apparatus for 2 hours in the same manner as described for the Bellafoline release.

After 60 and 120 minutes withdraw 10.0 ml. through a pipet with a glass-wool filter. Filter thorugh Number 1 Whatman filter paper, discarding the first portion. Dilute 3.0 ml. of the filtrate to 100.0 ml. with 0.1 N NH$_4$OH.

Each time a sample is withdrawn, replace the volume with SGF. At the end of each hour, also adjust the volume to 800 ml. before withdrawing the sample.

At the end of the second hour, proceed as described under SIF in (1) above.

Determine the absorbance of the samples with a suitable spectrophotometer between 300 nm. and 220 nm. in a 1 cm. cell using 0.1 N NH$_4$OH as a blank. The absorbance of 0.03 mg. phenobarbital/ml. 0.1 N NH$_4$OH in a 1 cm. cell at a maximum of about 240 nm. is 1.360.

The results of the test are as follows:

| SAMPLING TIME | PERCENT DRUG RELEASED PRESENT FORMULATION | PRIOR ART FORMULATION |
|---|---|---|
| 1 hr. | 35 –55 % phenobarbital 35 – 55 % bellafoline | 40 – 60 % phenobarbital 85 – 95 % bellafoline |
| 2 hrs. | 5 – 15 % phenobarbital 5 – 15 % bellafoline | 8 – 25 % phenobarbital 5 – 10 % |
| 3 hrs. | 5 – 15 % phenobarbital 5 – 15 % bellafoline | — — |
| 4 hrs. | 10 – 20 % phenobarbital | — |

| | PERCENT DRUG RELEASED | |
|---|---|---|
| SAMPLING TIME | PRESENT FORMULATION | PRIOR ART FORMULATION |
| | 10 – 20 %<br>bellafoline | —<br>— |

These results show the unobvious improved retardation of drug release for the formulations of the present invention over the existing prior art system of vinyl acetate-vinyl alcohol copolymer. An additional improvement is the greater uniformity of each drug component released per unit time.

EXAMPLE 4

Tablets prepared as described in Example 1 were tested for the dissolution rate of phenobarbital and bellafoline using the rotary bottle method, as described in the National Formulary, NFXII Second Supplement, p. 15, "Timed Release Tablets and Capsules - In Vitro Test Procedure." This dissolution test is run as follows:

(1) The tablets are rotated at 40 ±2 RPM and 37° C. in a bottle containing 50 ml. of simulated gastric fluid (0.1N Hcl).

(2) Aliquots are taken from the bottle at hourly intervals and analyzed for percent drug release.

The results of the test are as follows:

| | PERCENT DRUG RELEASED | |
|---|---|---|
| SAMPLING TIME | PRESENT FORMULATION | PRIOR ART FORMULATION |
| 1 hr. | 35 – 55 %<br>phenobarbital<br>30 – 55 %<br>bellafoline<br>30 – 55 %<br>ergotamine | 40 – 60 %<br>phenobarbital<br>85 – 95 %<br>bellafoline<br>60 – 80 %<br>ergotamine |
| 2 hrs. | 5 – 15 %<br>phenobarbital<br>5 – 20 %<br>bellafoline<br>5 – 20 %<br>ergotamine | —<br>—<br>— |

These results show the unobvious improved retardation of drug release for the formulations of the present invention over the existing prior art systems of vinyl acetate-vinyl alcohol copolymer. An additional improvement is the greater uniformity of each drug component released per unit time.

What is claimed is:

1. A three component sustained release medicament formulation comprising;
    a first component comprising phenobarbital and belladonna levoratory alkaloids incorporated into an immediate release portion;
    a second component comprising belladonna levoratory alkaloids incorporated into a separate basic pH affected controlled release matrix; with phenobarbital, microcrystalline cellulose, and calcium sulfate also incorporated into a separate control release vinyl acetate-vinyl alcohol copolymer resin matrix; and
    a third component comprising phenobarbital and belladonna levoratory alkaloids each incorporated into a separate control release vinyl acetate-vinyl alcohol copolymer resin matrix.

2. The formulation of claim 1, wherein the concentration of belladonna levoratory alkaloids in the second component is from about 1/10 to about 1/1000 of the total concentration of sustained release medicament formulations.

3. The formulation of claim 2, wherein the concentration of belladonna levoratory alkaloids in the second component is from 1/100 to 1/300 of the total concentration of the sustained release medicament formulation.

4. The formulation of claim 1, wherein the basic pH affected controlled release matrix is selected from the group consisting of cellulose acetate phthalate, polyvinyl acetate phthalate, and hydroxy propylmethyl cellulose phthalate.

5. The formulation of claim 4, wherein the basic pH affected controlled release matrix is cellulose acetate phthalate.

6. The formulation of claim 5, wherein insoluble salts of calcium sulfate or barium sulfate are incorporated into the basic pH affected controlled release matrix.

7. A three component sustained release medicament formulation comprising:
    a first component comprising, phenobarbital belladonna levoratory alkaloids and ergotamine incorporated into an immediate release portion;
    a second component comprising belladonna levoratory alkaloids and ergotamine incorporated into a separate basic pH affected controlled release matrix; with phenobarbital, microcrystalline cellulose and calcium sulfate also incorporated into a separate control release vinyl acetate-vinyl alcohol copolymer matrix; and
    a third component comprising phenobarbital and belladonna levoratory alkaloids ergotamine each incorporated into a separate control release vinyl-acetate vinyl alcohol copolymer resin matrix.

8. The formulation of claim 7, wherein the concentration of belladonna levoratory alkaloids and the ergotamine in the second component are each from about 1/10 to about 1/1000 of the total concentration of sustained release medicament formulation.

9. The formulation of claim 2, wherein the concentration of belladonna levoratory alkaloids and the ergotamine in the second component are from 1/100 to 1/300 of the total concentration of the sustained release medicament formulation.

10. The formulation of claim 7, wherein the basic pH affected controlled release matrix is selected from the group consisting of cellulose acetate phthalate, polyvinyl acetate phthalate, and hydroxy propylmethyl cellulose phthalate.

11. The formulation of claim 10, wherein the basic pH affected controlled release matrix is cellulose acetate phthalate.

12. The formulation of claim 11, wherein insoluble salts of calcium sulfate or barium sulfate are incorporated into the basic pH affected controlled release matrix.

* * * * *